Figure 1:
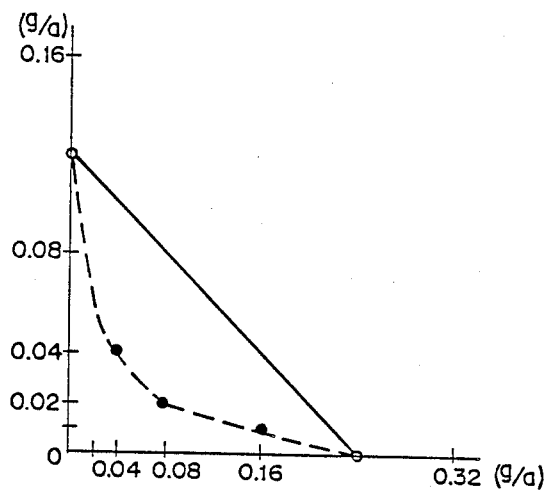

United States Patent [19]

Morita et al.

[11] Patent Number: 4,935,050

[45] Date of Patent: Jun. 19, 1990

[54] HERBICIDAL COMPOSITION

[75] Inventors: Kouichi Morita, Toyonaka; Ryo Yoshida, Kawanishi, both of Japan

[73] Assignee: Sumitomo Chemical Company, Limited, Osaka, Japan

[21] Appl. No.: 80,822

[22] Filed: Aug. 3, 1987

Related U.S. Application Data

[63] Continuation of Ser. No. 797,012, Nov. 12, 1985, abandoned.

[30] Foreign Application Priority Data

Nov. 12, 1984 [JP] Japan ................................ 59-237718
Nov. 13, 1984 [JP] Japan ................................ 59-238854
Nov. 13, 1984 [JP] Japan ................................ 59-238855

[51] Int. Cl.$^5$ ........................ A01N 43/42; A01N 43/38
[52] U.S. Cl. ............................................ 71/94; 71/96
[58] Field of Search ...................................... 71/94, 96

[56] References Cited

FOREIGN PATENT DOCUMENTS 0041603 4/1981 European Pat. Off. .
0083055 7/1983 European Pat. Off. .

*Primary Examiner*—Richard L. Raymond
*Assistant Examiner*—Mark W. Russell
*Attorney, Agent, or Firm*—Birch, Stewart, Kolasch & Birch

[57] ABSTRACT

A herbicidal composition which comprises as the active ingredients (a) 2-(4-chloro-2-fluoro-5-n-pentyloxy-carbonylmethoxyphenyl)-4,5,6,7-tetrahydro- -2H-isoindole-1,3-dione and (b) at least one of methyl 5-(2-chloro-4-trifluoromethylphenoxy)-2-nitroacetophenoneoxime-O-acetate (PPG-1013), 1-(carboethoxy)ethyl 5-[2-chloro-4-trifluoromethyl)phenyl]-2-nitrobenzoate (lactofen) and 2-[4,5-dihydro-4-methyl-4-(1-methylethyl)-5-oxo-1H-imidazol-2-yl]-3-quinolinecarboxylic acid (imazaquin), and an inert carrier or diluent. Said composition exerts an enhanced herbicidal potency.

5 Claims, 1 Drawing Sheet

HERBICIDAL COMPOSITION

This application is a continuation of copending application Ser. No. 797,012, filed on Nov. 12, 1985 now abandoned.

The present invention relates to a herbicidal composition. More particularly, it relates to a herbicidal composition comprising as the active ingredients (a) 2-(4-chloro-2-fluoro-5-n-pentyloxycarbonylmethoxyphenyl)-4,5,6,7-tetrahydro-2H-isoindole-1,3-dione (hereinafter referred to as "Compound (I)") of the formula:

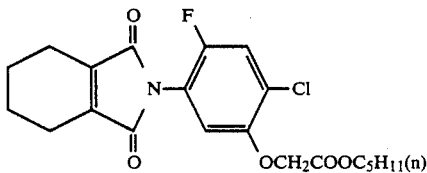

and (b) at least one of methyl 5-(2-chloro-4-trifluoromethylphenoxy)-2-nitroacetophenonoxime-O-acetate (hereinafter referred to as "PPG-1013") of the formula:

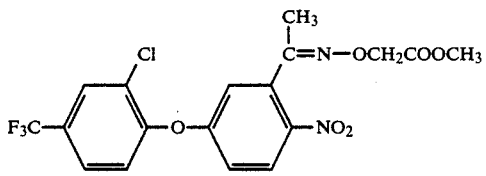

1-(carboethoxy)ethyl 5-[2-chloro-4-(trifluoromethyl)-phenoxy]-2-nitrobenzoate (hereinafter referred to as "lactofen") of the formula:

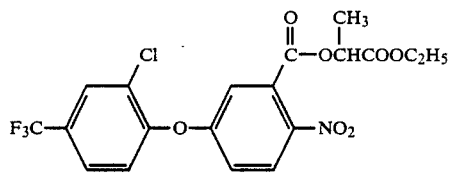

and 2-[4,5-dihydro-4-methyl-4-(1-methylethyl)-5-oxo-1H-imidazol-2-yl]-3-quinolinecarboxylic acid (hereinafter referred to as "imazaquin") of the formula:

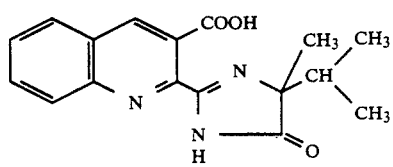

which exerts a highly enhanced herbicidal activity against a wide variety of weeds without causing any material phytotoxicity to crop plants, particularly to peanut and soybean.

In recent years, a great number of chemicals having herbicidal activities have been used in order to exterminate or control the undesired vegetation of weeds. Since, however, weeds are diversified in kinds and grow over a long period of time, the herbicidal effects of conventional herbicidal agents are restricted in general. In view of such situation, the appearance of any herbicidal agent which exerts a strong herbicidal activity against a wide variety of weeds without any material phytotoxicity to crop plants has been highly demanded.

As a result of the extensive study, it has now been found that the associated use of (a) Compound (I) with (b) at least one of PPG-1013, lactofen and imazaquin, these being hereinafter referred to as "Compounds (II)", produces a highly enhanced herbicidal activity against a wide variety of weeds without causing any material phytotoxicity to crop plants, particularly peanut or soybean. In comparison with the sole use of each of said active ingredients, enhancement of the herbicidal potency on such associated use is remarkable so that the active ingredients may be applied in smaller dosages. Thus, a clear and definite synergistic effect is observed in said associated use.

The herbicidal composition of the invention can exterminate or control a variety of weeds, i.e. dicotyledonous weeds such as common lambsquarters (*Chenopodium album*), redroot pigweed (*Amaranthus retroflexus*), common purslane (*Portulaca oleracea*), common cocklebur (*Xanthium strumarium*), jimsonweed (*Datura stramonium*) and velvetleaf (*Abutilon theophrasti*), Ipomoea plants such as tall morningglory (*Ipomoea purpurea*), hemp sesbania (*Sesbania exaltata*), prickly sida (*Sida spinosa*), black nightshade (*Solanum nigrum*) and common sunflower (*Helianthus annuus*), monocotyledonous weeds such as green foxtail (*Setaria viridis*), southern crabgrass (*Digitaria ciliaris*), barnyardgrass (*Echinochloa crus-galli*) and johnsongrass (*Sorghum halepense*), quackgrass (*Agropyron repens*), etc.

Compound (I) is known to exert a herbicidal activity [EP-A No. 0083055]. Compounds (II), i.e. PPG-1013 (U.S. Pat. No. 4,344,789); lactofen (EP-A No. 0020052) and imazaquin [EP-A No. 0041623], are also known to have a herbicidal activity. However, the associated use of Compound (I) with any of Compounds (II) has never been attempted, and the production of said synergistic effect on such associated use has never been expected.

The proportion of Compound (I) as the component (a) and Compound(s) (II) as the component (b) in the composition of the invention may vary in a considerably broad range, usually from 1:0.005 to 1:50 by weight. When Compound (II) is PPG-1013, its amount may be preferably from 0.005 to 10 parts by weight, especially from 0.025 to 5 parts by weight, to one part by weight of Compound (I). When lactofen is used as Compound (II), its amount may be favorably from 0.2 to 50 parts by weight, particularly from 0.2 to 20 parts by weight, to one part by weight of Compound (I). In case of Compound (II) being imazaquin, it may be used preferably in an amount of from 0.2 to 50 parts by weight, especially from 0.5 to 20 parts by weight, to one part by weight of Compound (I).

In addition to the above active ingredients, the composition may contain a solid or liquid carrier or diluent. Any surface active or auxiliary agent may be also contained therein. Thus, the composition may be formulated in any conventional preparation form such as emulsifiable concentrate, wettable powder or suspension. The total content of the active ingredients, i.e. Compound (I) and Compound(s) (II), may be from 0.5 to 90% by weight, preferably from 1 to 80% by weight.

As the solid carrier or diluent, there may be used kaolin clay, attapulgite clay, bentonite, terra alba, pyrophyllite, talc, diatomaceous earth, calcite, wallnut-shell powder, urea, ammonium sulfate, synthetic hydrated silica, etc. Examples of the liquid carrier or diluent are aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (e.g. soybean oil, cotton-seed oil), dimethylsulfoxide, acetonitrile, water, etc.

The surface active agent used for emulsification, dispersion or spreading may be any of the anionic and nonionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the composition are illustratively shown in the following Formulation Examples wherein part(s) are by weight.

FORMULATION EXAMPLE 1

Ten parts of Compound (I), 10 parts of PPG-1013, lactofen or imazaquin, 10 parts of synthetic hydrated silica, 3 parts of alkylsulfate, 2 parts of calcium ligninsulfonate and 65 parts of diatomaceous earth are well mixed and pulverized to obtain a wettable powder.

FORMULATION EXAMPLE 2

0.5 part of Compound (I), 1.5 parts of PPG-1013, lactofen or imazaquin, 1 part of synthetic hydrated silica, 2 parts of calcium ligninsulfonate, 30 parts of bentonite and 65 parts of kaolin clay are well mixed and pulverized. The resulting powder is admixed with water and dried to obtain granules.

FORMULATION EXAMPLE 3

Forty parts of Compound (I), 40 parts of imazaquin, 3 parts of calcium ligninsulfonate, 2 parts of sodium laurylsulfate and 15 parts of synthetic hydrated silica are well mixed and pulverized to obtain a wettable powder.

FORMULATION EXAMPLE 4

1.5 Parts of Compound (I), 0.5 part of PPG-1013 or lactofen, 1 part of polyoxyethylene sorbitan monooleate, 5 parts of polyvinyl alcohol and 92 parts of water are mixed and pulverized until the particle size of the composition become less than 5 microns to obtain suspensions.

FORMULATION EXAMPLE 5

Four parts of Compound (I), 2 parts of PPG-1013, 14 parts of polyoxyethylenestyryl phenyl ether, 6 parts of calcium dodecylbenzenesulfonate, 34 parts of xylene and 40 parts of cyclohexanone are well mixed to obtain an emulsifiable concentrate.

A composition comprising Compound (I) and Compound(s) (II) thus formulated is useful for post-emergence control of undesired weeds by foliar treatment. The foliar treatment may be effected by spraying the composition containing Compound (I) and Compound(s) (II) over the top of plants. The direct application may also be adopted.

In order to improve the herbicidal activity, the composition may be used with other herbicides. Besides, it may be used in combination with insecticides, acaricides, nematocides, fungicides, plant growth regulators, fertilizers, soil improvers, etc.

The dosage of the active ingredients may vary depending on prevailing weather conditions, soil involved, formulation used, mixing proportion of each active ingredient, crop and weed species, etc. In general, however, the total amount of Compound (I) and Compound(s) (II) is within a range of about 0.1 to 10 grams per are. When Compound (II) is PPG-1013, said total amount is preferred to be from about 0.2 to 4 grams per are. When Compound (II) is lactofen, said total amount may be favorably from about 0.1 to 10 grams per are. When Compound (II) is imazaquin, said total amount may be preferably from about 0.5 to 10 grams per are.

In case of the composition being formulated into an emulsifiable concentrate, wettable powder or suspension, it is normally diluted with water and applied over the top at a volume of about 1 to 10 liters per are to the foliage of the crop plants or weeds which germinate or have germinated. The dilution may include, in addition to the above mentioned surface active agent, any spreading or auxiliary agent such as polyoxyethylene resin acid esters, ligninsulfonates, abietic acid, dinaphthylmethanedisulfonates, paraffin and the like.

The practical herbicidal activity of the system of the invention will be explained in further detail with reference to the following Test Examples wherein the growth controlling percentage (%) was determined by weighing the aerial parts of the test plants (fresh weight) and making calculation according to the following equation:

$$\text{Growth controlling percentage (\%)} = \left\{ 1 - \frac{\text{Fresh weight of test plant in treated plot}}{\text{Fresh weight of test plant in untreated plot}} \right\} \times 100$$

The phytotoxicity to crop plants was visually observed.

TEST EXAMPLE 1

Seeds of common cocklebur, tall morningglory, velvetleaf, hemp sesbania, field bindweed and soybean were sowed in a concrete pot (40×35 cm², 35 cm (H)) filled with field soil and the test plants were grown for 15 days in outdoors. A designed amount of the composition in the form of a wettable powder formulated as in Formulation Example 1 was diluted with water containing a spreading agent and sprayed to the foliage of the test plants at a spray volume of 5 liters per are by the aid of a small hand sprayer. After 21 days' cultivation in outdoors, the growth controlling percentage was observed. The results are shown in Table 1. At the time of treatment, the test plants were in general at 1.5 to 4-leaf stage, although the growing stage varied depending on each species.

TABLE 1

| Compound No. | Dosage (g/a) | Mixing ratio | Growth controlling percentage (%) | | | | | Phyto-toxicity Soybean |
|---|---|---|---|---|---|---|---|---|
| | | | Common cocklebur | Tall morning-glory | Velvet-leaf | Hemp sesbania | Field bind-weed | |
| Compound (I) | 4 | — | 100 | 93 | 95 | 91 | 100 | None |
| | 2 | — | 100 | 85 | 95 | 72 | 100 | None |
| | 1 | — | 83 | 83 | 93 | 53 | 100 | None |
| | 0.5 | — | 75 | 68 | 85 | 34 | 93 | None |
| | 0.2 | — | 40 | 40 | 85 | 15 | 70 | None |
| PPG-1013 | 0.8 | — | 100 | 100 | 100 | 100 | 100 | None |
| | 0.4 | — | 100 | 100 | 100 | 100 | 98 | None |
| | 0.2 | — | 95 | 65 | 100 | 90 | 90 | None |
| | 0.1 | — | 40 | 45 | 100 | 48 | 60 | None |
| | 0.05 | — | 20 | 20 | 80 | 20 | 30 | None |
| Compound (I) + PPG-1013 | 0.2 + 0.05 | 4:1 | 65 | 65 | 98 | 51 | 90 | None |
| | 0.2 + 0.1 | 2:1 | 81 | 89 | 100 | 77 | 100 | None |
| | 0.2 + 0.2 | 1:1 | 99 | 95 | 100 | 98 | 100 | None |
| | 0.2 + 0.4 | 1:2 | 100 | 100 | 100 | 100 | 100 | None |
| | 0.5 + 0.05 | 10:1 | 96 | 90 | 100 | 61 | 100 | None |
| | 0.5 + 0.1 | 5:1 | 99 | 97 | 100 | 83 | 100 | None |
| | 0.5 + 0.2 | 5:2 | 100 | 100 | 100 | 99 | 100 | None |
| | 0.5 + 0.4 | 5:4 | 100 | 100 | 100 | 100 | 100 | None |
| | 1 + 0.05 | 20:1 | 99 | 97 | 100 | 79 | 100 | None |
| | 1 + 0.1 | 10:1 | 100 | 100 | 100 | 93 | 100 | None |
| | 1 + 0.2 | 5:1 | 100 | 100 | 100 | 100 | 100 | None |
| | 1 + 0.4 | 5:2 | 100 | 100 | 100 | 100 | 100 | None |
| | 2 + 0.05 | 40:1 | 100 | 100 | 100 | 100 | 100 | None |
| | 2 + 0.1 | 20:1 | 100 | 100 | 100 | 100 | 100 | None |
| | 2 + 0.2 | 10:1 | 100 | 100 | 100 | 100 | 100 | None |
| | 2 + 0.4 | 5:1 | 100 | 100 | 100 | 100 | 100 | None |
| Untreated | | | 0 | 0 | 0 | 0 | 0 | None |

TEST EXAMPLE 2

Seeds of field bindweed, velvetleaf, jimsonweed, redroot pigweed, black nightshade and soybean were sowed in a vat (33×23 cm², 11 cm (H)) filled with field soil and the test plants were grown for 18 days in outdoors. A designed amount of the composition in the form of a wettable powder formulated as in Formulation Example 1 was diluted with water containing a spreading agent and sprayed to the foliage of the test plants at a spray volume of 5 liters per are by the aid of a small hand sprayer. After 20 days' cultivation in outdoors, the growth controlling percentage was observed. The results are shown in Table 2. At the time of treatment, the test plants were in general at 1 to 4-leaf stage, although the growing stage varied depending on each species.

TEST EXAMPLE 3

Seeds of tall morningglory, velvetleaf, jimsonweed, redroot pigweed, black nightshade and soybean were sowed in a plastic pot (11 cm (diameter), 8 cm (H)) filled with field soil and the test plants were grown for 14 days in a greenhouse. A designed amount of the composition in the form of a wettable powder formulated as in Formulation Example 1 was diluted with water containing a spreading agent and sprayed to the foliage of the test plants at a spray volume of 5 liters per are by the aid of a small hand sprayer. After 14 days' cultivation in the greenhouse, the growth controlling percentage was observed. The results are shown in Table 3. At the time of treatment, the test plants were in general at 1 to 3-leaf stage, although the growing stage varied depending on each species.

TABLE 2

| Compound No. | Dosage (g/a) | Mixing ratio | Growth controlling percentage (%) | | | | | Phyto-toxicity Soybean |
|---|---|---|---|---|---|---|---|---|
| | | | Field bindweed | Velvet-leaf | Jimson-weed | Redroot pigweed | Black night-shade | |
| Compound (I) + Lactofen | 1 + 0.5 | 1:0.5 | 100 | 100 | 100 | 100 | 100 | None |
| Untreated | | | 0 | 0 | 0 | 0 | 0 | None |

TABLE 3

| Compound No. | Dosage (g/a) | Mixing ratio | Growth controlling percentage (%) | | | | | Phyto-toxicity Soybean |
|---|---|---|---|---|---|---|---|---|
| | | | Tall morning-glory | Velvet-leaf | Jimson-weed | Redroot pigweed | Black night-shade | |
| Compound (I) | 0.5 | — | 85 | 90 | 83 | 95 | 90 | None |
| Lactofen | 0.5 | — | 43 | 75 | 70 | 90 | 90 | None |
| Compound (I) + Lactofen | 0.5 + 0.5 | 1:1 | 100 | 100 | 100 | 100 | 100 | None |

TABLE 3-continued

| Compound No. | Dosage (g/a) | Mixing ratio | Tall morning-glory | Velvet-leaf | Jimson-weed | Redroot pigweed | Black night-shade | Phyto-toxicity Soybean |
| --- | --- | --- | --- | --- | --- | --- | --- | --- |
| Untreated | | | 0 | 0 | 0 | 0 | 0 | None |

Growth controlling percentage (%)

TEST EXAMPLE 4

Seeds of common lambsquarters, prickly sida, velvetleaf, redroot pigweed, black nightshade and soybean were sowed in a vat ($33 \times 23$ cm$^2$, 11 cm (H)) filled with field soil and the test plants were grown for 18 days in outdoors. A designed amount of the composition in the form of a wettable powder formulated as in Formulation Example 1 was diluted with water containing a spreading agent and sprayed to the foliage of the test plants at a spray volume of 5 liters per are by the aid of a small hand sprayer. After 20 days' cultivation in outdoors, the growth controlling percentage was observed. The results are shown in Table 4. At the time of treatment, the test plants were in general at 1 to 4-leaf stage, although the growing stage varied depending on each species.

TABLE 4

| Compound No. | Dosage (g/a) | Mixing ratio | Common lambs-quarters | Prickly sida | Velvet-leaf | Redroot pigweed | Black night-shade | Phyto-toxicity Soybean |
| --- | --- | --- | --- | --- | --- | --- | --- | --- |
| Compound (I) + Imazaquin | 1 + 1 | 1:1 | 100 | 100 | 100 | 100 | 100 | None |
| Untreated | | | 0 | 0 | 0 | 0 | 0 | None |

Growth controlling percentage (%)

TEST EXAMPLE 5

Seeds of velvetleaf, common lambsquarters, black nightshade, prickly sida and soybean were sowed in a plastic pot (11 cm (diameter), 8 cm (H)) filled with field soil and the test plants were grown for 14 days in a greenhouse. A designed amount of the composition in the form of a wettable powder formulated as in Formulation Example 1 was diluted with water containing a spreading agent and sprayed to the foliage of the test plants at a spray volume of 5 liters per are by the aid of a small hand sprayer. After 14 days' cultivation in the greenhouse, the growth controlling percentage was observed. The results are shown in Table 5. At the time of treatment, the test plants were in general at 1 to 3-leaf stage, although the growing stage varied depending on each species.

TABLE 5

| Compound No. | Dosage (g/a) | Mixing ratio | Velvetleaf | Common lambs-quarters | Black night-shade | Prickly sida | Phyto-toxicity Soybean |
| --- | --- | --- | --- | --- | --- | --- | --- |
| Compound (I) | 0.5 | — | 90 | 85 | 90 | 85 | None |
| Imazaquin | 0.5 | — | 30 | 70 | 60 | 80 | None |
| Compound (I) + Imazaquin | 0.5 + 0.5 | 1:1 | 100 | 100 | 100 | 100 | None |
| Untreated | | | 0 | 0 | 0 | 0 | None |

Growth controlling percentage (%)

TEST EXAMPLE 6

Seeds of velvetleaf were sowed in a plastic pot ($11 \times 15$ cm$^2$, 7 cm (H)) filled with field soil and the test plant was grown for 21 days in outdoors. A designed amount of the composition in the form of a wettable powder formulated as in Formulation Example 1 was diluted with water and sprayed to the foliage of the test plant at a spray volume of 4 liters per are by the aid of a small hand sprayer. After 22 days' cultivation in outdoors, the growth controlling percentage was observed. The results are shown in Table 6. At the time of treatment, the test plant was 3-leaf stage and in 5 cm height.

TABLE 6

| Dosage of PPG-1013 (g/a) | Dosage of Compound (I) (g/a) Growth controlling percentage (%) | | | | |
| --- | --- | --- | --- | --- | --- |
| | 0 | 0.04 | 0.08 | 0.16 | 0.32 |
| 0 | 0 | 30 | 50 | 80 | 100 |
| 0.02 | 30 | 75 | 90 | 100 | 100 |
| 0.04 | 50 | 90 | 100 | 100 | 100 |
| 0.08 | 80 | 100 | 100 | 100 | 100 |
| 0.16 | 100 | 100 | 100 | 100 | 100 |

The above test results were analyzed according to the equivalent efficacy streaking method (cf. Hideo Chisaka: "Noyaku Jikkenho" (Agricultural Expeirmental Method), Chapter 3: Herbicides, pages 109–116). Namely, several combinations of the compositions having different mixing ratio of Compounds (I) and PPG-1013 but exerting the same level of growth controlling effect, for example, 90% growth control, were analyzed and plotted in a graph so as to readily determine a synergistic effect, arithmetic effect or competitive effect. In case of enhancing the synergistic effect, the equivalent efficacy line as plotted is shown below the arithmetic efficacy line.

As shown in FIG. 1 of the accompanying drawing wherein the ordinate indicates the dosage of PPG-1013 per are and the abscissa indicates the dosage of Compound (I) per are, the equivalent efficacy line (e.g. dotted line) of 90% growth control of velvetleaf is located under the arithmetic efficacy line (e.g. solid line), from which it is presumed revealed that the associated use of Compound (I) and PPG-1013 in certain mixing ratio would enhance the synergistic effect.

TEST EXAMPLE 7

Seeds of velvetleaf were sowed in a plastic pot ($11 \times 15$ cm$^2$, 7 cm (H)) filled with field soil and the test plant was grown for 21 days in outdoors. A designed amount of the composition in the form of a wettable powder formulated as in Formulation Example 1 was diluted with water and sprayed to the foliage of the test plant at a spray volume of 4 liters per are by the aid of a small hand sprayer. After 22 days' cultivation in outdoors, the growth controlling percentage was observed. The results are shown in Table 7. At the time of treatment, the test plant was 3-leaf stage and in 5 cm height.

TABLE 7

| Dosage of lactofen (g/a) | Dosage of Compound (I) (g/a) Growth controlling percentage (%) | | | | |
|---|---|---|---|---|---|
| | 0 | 0.04 | 0.08 | 0.16 | 0.32 |
| 0 | 0 | 30 | 50 | 80 | 100 |
| 0.16 | 20 | 50 | 70 | 100 | 100 |
| 0.32 | 45 | 70 | 90 | 100 | 100 |
| 0.64 | 60 | 90 | 100 | 100 | 100 |
| 1.28 | 90 | 100 | 100 | 100 | 100 |

The above test results were analyzed according to the equivalent efficacy streaking method (cf. Hideo Chisaka: "Noyaku Jikkenho" (Agricultural Expeirmental Method), Chapter 3: Herbicides, pages 109–116). Namely, several combinations of the compositions having different mixing ratio of Compound (I) and lactofen but exerting the same level of growth controlling effect, for example, 90% growth control, were analyzed and plotted in a graph so as to readily determine a synergistic effect, arithmetic effect or competitive effect. In case of enhancing the synergistic effect, the equivalent efficacy line as plotted is shown below the arithmetic efficacy line.

Figure 2:
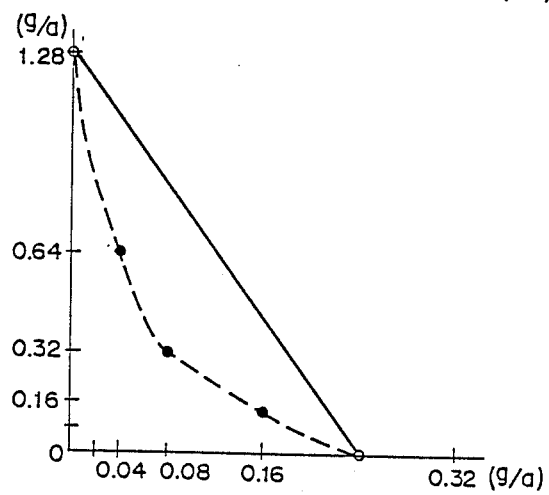

As shown in FIG. 2 of the accompanying drawing wherein the ordinate indicates the dosage of lactofen per are and the abscissa indicates the dosage of Compound (I) per are, the equivalent efficacy line (e.g. dotted line) of 90% growth control of velvetleaf is located under the arithmetic efficacy line (e.g. solid line), from which it is presumed revealed that the associated use of Compound (I) and lactofen in certain mixing ratio would ehhance the synergistic effect.

TEST EXAMPLE 8

Seeds of redroot pigweed were sowed in a plastic pot ($11 \times 15$ cm$^2$, 7 cm (H)) filled with field soil and the test plant was grown for 21 days in outdoors. A designed amount of the composition in the form of a wettable powder formulated as in Formulation Example 1 was diluted with water and sprayed to the foliage of the test plant at a spray volume of 4 liters per are by the aid of a small hand sprayer. After 22 days' cultivation in outdoors, the growth controlling percentage was observed. The results are shown in Table 8. At the time of treatment, the test plant was 3-leaf stage and in 3 cm height.

TABLE 8

| Dosage of imazaquin (g/a) | Dosage of Compound (I) (g/a) Growth controlling percentage (%) | | | | |
|---|---|---|---|---|---|
| | 0 | 0.04 | 0.08 | 0.16 | 0.32 |
| 0 | 0 | 28 | 40 | 80 | 100 |
| 0.4 | 33 | 70 | 90 | 100 | 100 |
| 0.8 | 50 | 90 | 100 | 100 | 100 |
| 1.6 | 80 | 100 | 100 | 100 | 100 |
| 3.2 | 100 | 100 | 100 | 100 | 100 |

The above test results were analyzed according to the equivalent efficacy streaking method (cf. Hideo Chisaka: "Noyaku Jikkenho" (Agricultural Expeirmental Method), Chapter 3: Herbicides, pages 109–116). Namely, several combinations of the compositions having different mixing ratio of Compounds (I) and imazaquin but exerting the same level of growth controlling effect, for example, 90% growth control, were analyzed and plotted in a graph so as to readily determine a synergistic effect, arithmetic effect or competitive effect. In case of enhancing the synergistic effect, the equivalent efficacy line as plotted is shown below the arithmetic efficacy line.

Figure 3:
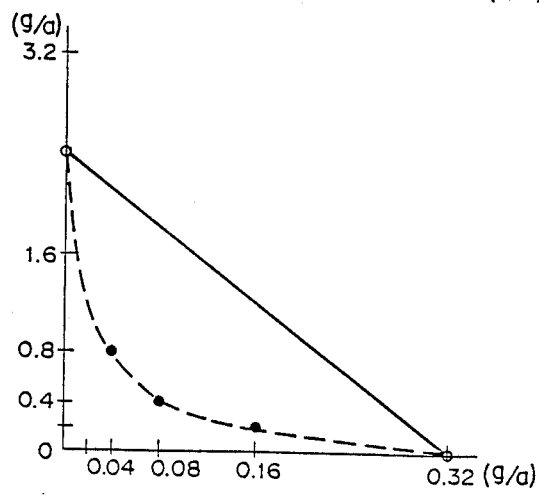

As shown in FIG. 3 of the accompanying drawing wherein the ordinate indicates the dosage of imazaquin per are and the abscissa indicates the dosage of Compound (I) per are, the equivalent efficacy line (e.g. dotted line) of 90% growth control of redroot pigweed is located under the arithmetic efficacy line (e.g. solid line), from which it is presumed revealed that the associated use of Compound (I) and imazaquin in certain mixing ratio would ehhance the synergistic effect.

What is claimed is:

1. A herbicidal composition which as the active ingredients consists essentially of (a) 2-(4-chloro-2-fluoro-5-n-pentyloxycarbonylmethoxyphenyl)-4,5,6,7-tetrahydro-2H-isoindole-1,3,-dione and (b) 2-[4,5-dihydro-4-methyl-4-(1-methylethyl)-5-oxo-1H-imidazol-2-yl]-3-quinolinecarboxylic acid (imazaquin), and an inert carrier or diluent, wherein the weight proportion of the components (a) and (b) is from 1:0.2 to 1:50.

2. A method for controlling weeds which comprises applying a herbicidally effective amount of the composition according to claim 1 to the weeds.

3. The method according to claim 2, wherein the weeds are those germinated in the field of peanut or soybean.

4. The method according to claim 2, wherein the total amount of the components (a) and (b) is from 0.1 to 10 grams per are.

5. The method according to claim 4, wherein said total amount is from 0.5 to 10 grams per are.

* * * * *